US00PP11240P

United States Patent [19]

Gass

[11] Patent Number: Plant 11,240

[45] Date of Patent: Feb. 22, 2000

[54] BACCHARIS PLANT NAMED 'STARN'

[76] Inventor: Ronald E. Gass, 5761 N. 105th La., Glendale, Ariz. 85304

[21] Appl. No.: 09/012,523

[22] Filed: Jan. 23, 1998

[51] Int. Cl.[7] ..... A01H 5/00

[52] U.S. Cl. ..... Plt./226

[58] Field of Search ..... Plt./226

*Primary Examiner*—Howard J. Locker
*Assistant Examiner*—Kent L. Bell
*Attorney, Agent, or Firm*—Joseph H. Roediger

[57] ABSTRACT

A new and distinct variety of the Baccharis plant named 'Starn' is provided. The new variety was selected as a single plant from a block of hybrid seedlings. The new variety is a staminate plant that does not produce the white floss (pappus) and seed associated in large quantity with Baccharis plants. The new variety is heat tolerant, possesses drought resistance, exhibits procumbent growth habit and displays green foliage coloration. The characteristics of this new variety of plant make it particularly well-suited for growing as a ground cover in urban desert landscapes and regions with limited water supply.

2 Drawing Sheets

SUMMARY OF THE INVENTION

The present invention comprises a new and distinct variety of Baccharis and hereinafter is referred to by the variety name 'Starn'. THOMPSON is a Trade Mark applied to the variety to indicate the source of origin thereof.

The new 'Starn' variety was selected by me as a single plant from a block of hybrid seedlings during the course of plant selection work conducted during the years 1985 and 1986. The hybrid seedlings were a result of a cross between the 'Centennial' Baccharis Plant and an unnamed parent. The 'Centennial' plant is an unpatented F1 hybrid resulting from crossing the Arizona native desert broom (*Baccharis sarothroides*) with the California native coyote bush (*Baccharis pilularis*) and was introduced by the University of Arizona, Tucson, Ariz. as reported in the article entitled "Development of Hybrid Baccharis Plants for Desert Landscaping" by A. E. Thompson et al., HortScience, Vol. 30 (7), Dec., 1995, Page 1357. The 'Centennial' Baccharis is the female parent and an unnamed *Baccharis sarothroides* was the pollen parent in the backcross that yielded the seedling which is the Baccharis plant 'Starn', the subject of this application.

Baccharis 'Starn' is distinguishable from 'Centennial' by producing only staminate (male) flowers while 'Centennial' produces only pistillate (female) flowers. Baccharis 'Starn' is distinguishable from the unnamed *Baccharis sarothroides* parent plant by distinctive vegetative growth. 'Starn' is a low, mounding, evergreen shrub which branches heavily and is dense in habit. Young 'Starn' plants under 12 inches tall have prostrate branches. In contrast, the parent is a broom-like shrub from 6 to 12 feet in height with numerous erect, angled branches. As a seedling under 12 inches tall, the parent exhibits an erect, open growth habit.

The seedlings were grown for about one year and a first selection was made based on low growth habit and fullness of branching structure. The selected seedlings were grown for three additional years and a superior growing staminate plant which had a desirable degree of procumbency and vigor was distinguished by these characteristics from the other seedlings. The selection of the staminate second generation Baccharis hybrid eliminates the generation of pappus and seeds further distinguishing this new plant from other Baccharis plants known to the inventor.

Asexual propagation of this new variety was carried out in Glendale, Ariz. by cuttings through several generations.

The desirable characteristics remain fixed in each successive crop of cutting-grown plants.

BRIEF DESCRIPTION OF THE DRAWINGS

The accompanying photographic drawings show typical specimens of plant parts of the new variety in color illustrations as nearly true as is reasonably possible to accomplish from conventional photographic procedures.

Figure 1:
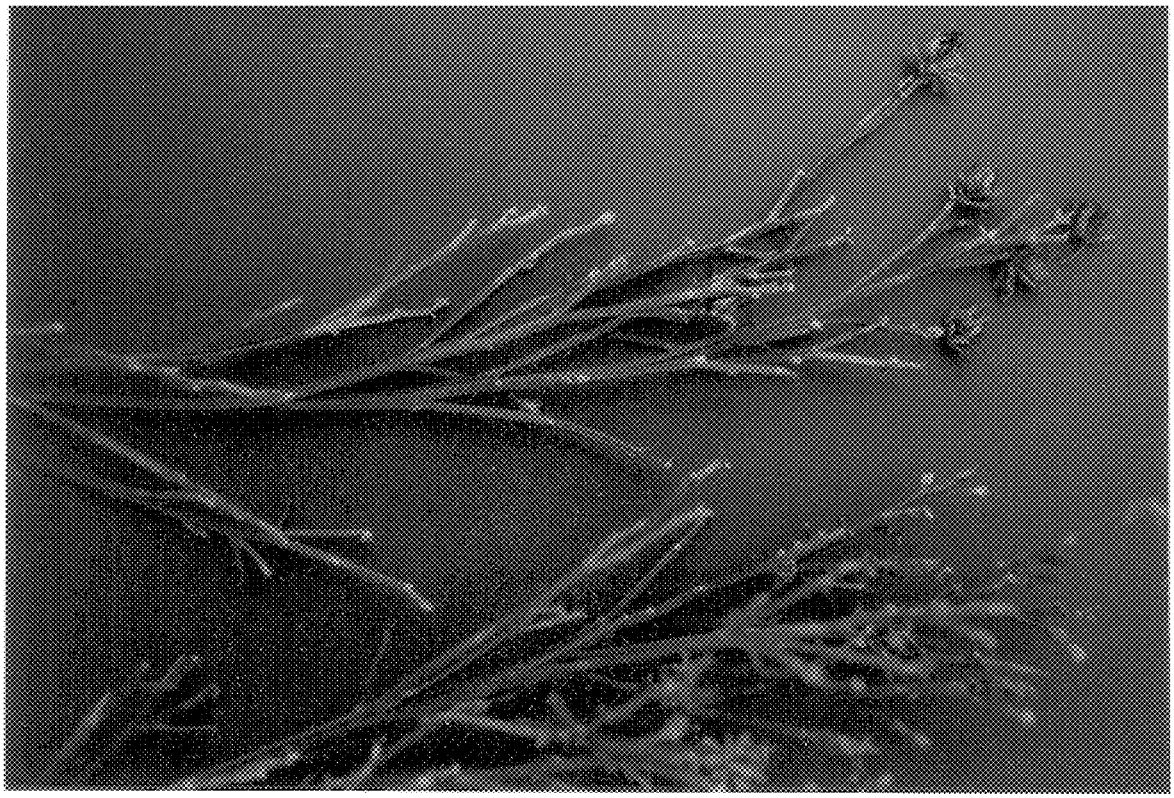
FIG. 1 shows male capitula at tips of branches in a dried state as they appear January–February. It also shows the branches with the previous years after most leaves have gone deciduous.
Figure 2:
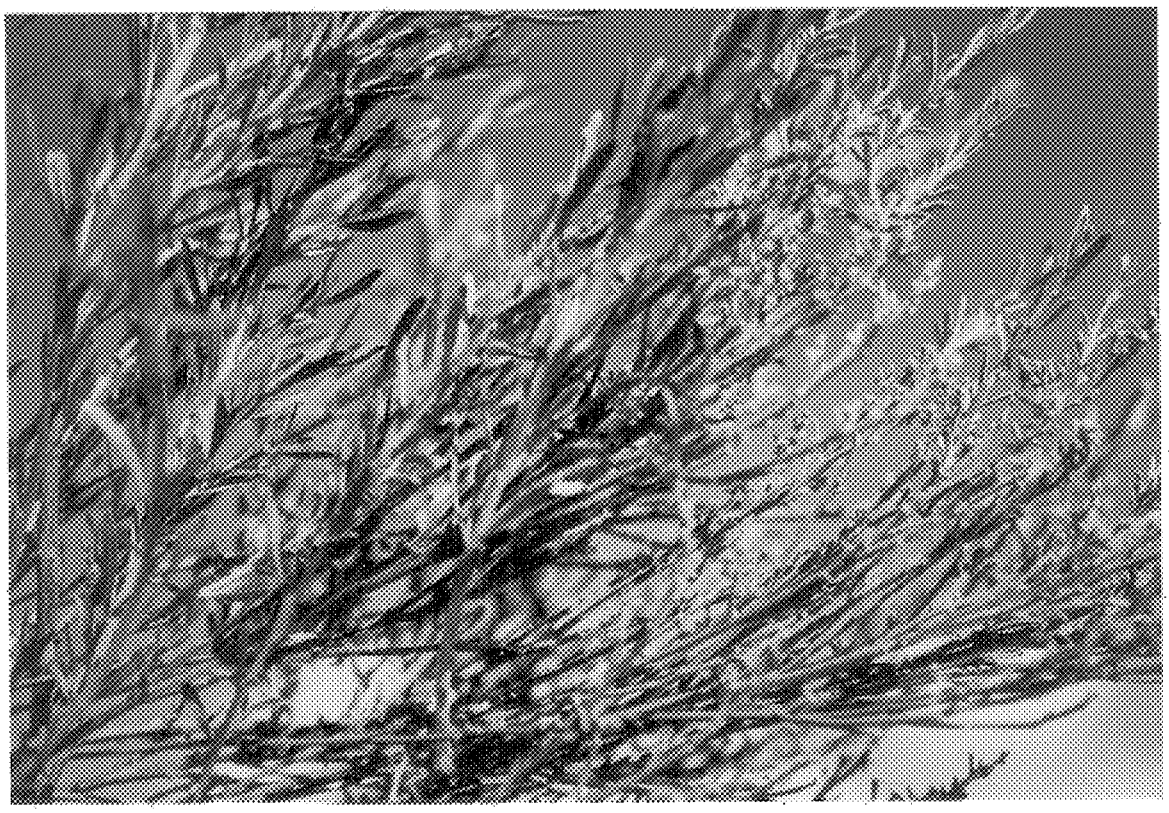
FIG. 2 shows the leaves and branches as growth begins in late February to early March.
Figure 3:
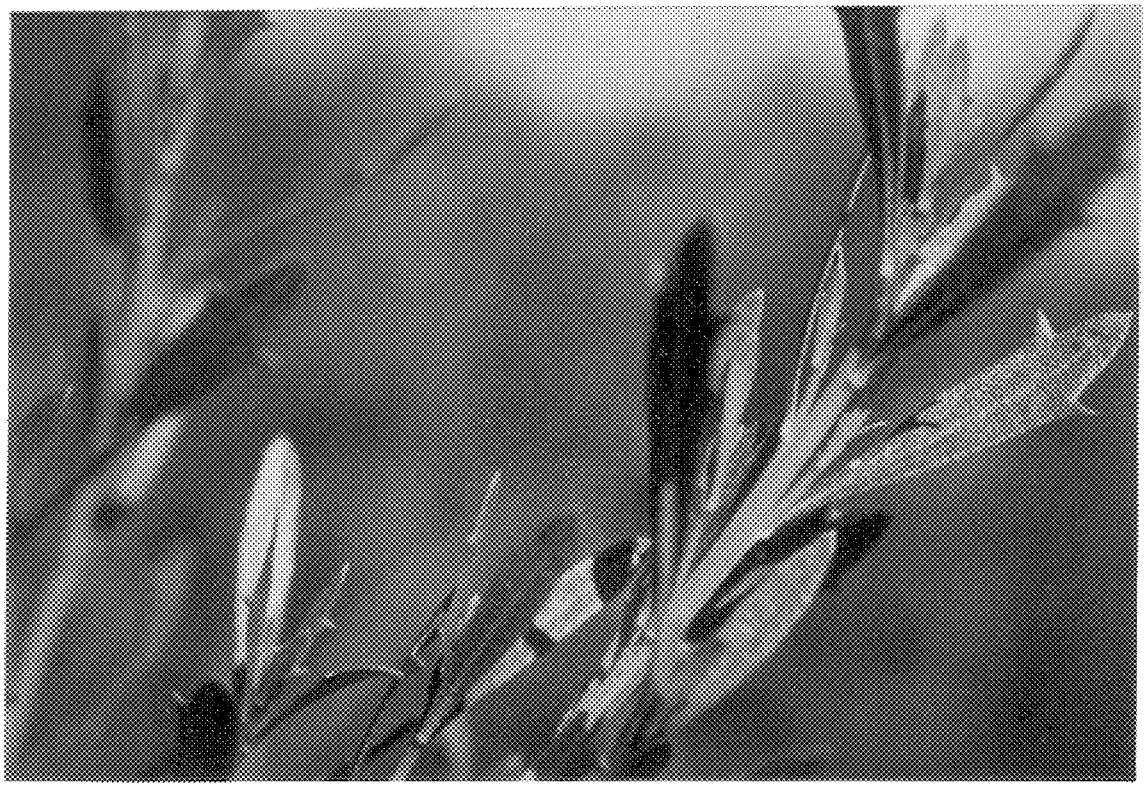
FIG. 3 shows a close-up view of the sparse teeth on the margin of the leaf sides.
Figure 4:
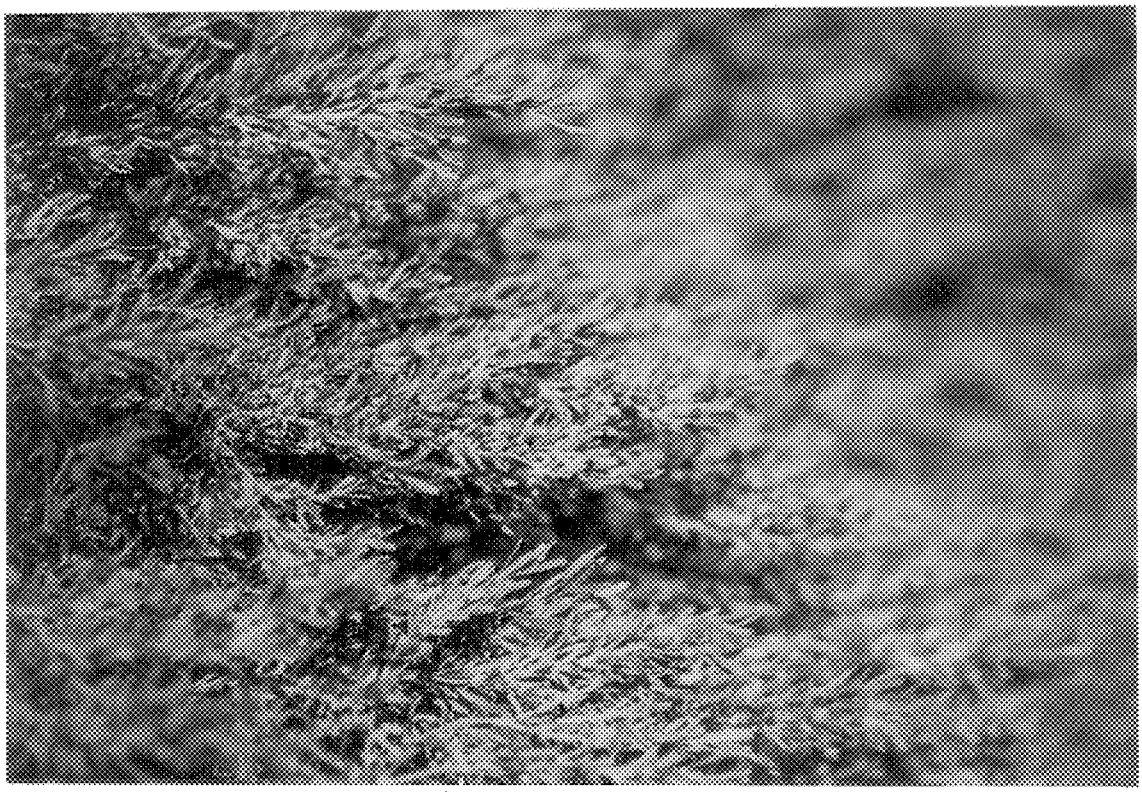
FIG. 4 shows the density of the procumbent shrub.

The color chart used in the identification of colors described hereinafter is the R.H.S. Colour Chart of The Royal Horticultural Society, London, England (or Pantone Color Series). The plants described were grown during 1996 at Glendale, Ariz.

Classification: Baccharis hybrid.
Plant form: Procumbent shrub.
Plant growth habit: Perennial.
Foliage:
- *Leaf arrangement*.—Alternate.
- *Leaf shape*.—Spathulate.
- *Leaf length*.—Early spring, leaves — 5.3 centimeters long. Summer leaves 1.3–2.3 centimeter. Autumn leaves 0.4 centimeters.
- *Leaf width*.—Early spring 1.5 centimeters wide. Summer 0.3–0.5 centimeters. Autumn 0.1 centimeters.
- *Leaf blade color*.—Uniform on all surfaces and edges. The closest match with the R.H.S. Colour Chart was in the yellow-green group #147 B. This color showed the closest match in all seasons of the year.
- *Leaf blade margin*.—Few teeth to entire Branches: Spring coloration of new growth is matched to R.H.S. #145A. Summer, autumn and winter coloration is match to R.H.S. #147C.
Inflorescence:
- *Male capitula*.—Inflorescence length 0.6 centimeters. Inflorescence width 0.6 centimeters.
- *Flower number*.—About 35 per capitula.

*Flower shape*.—Narrow, Tubular.

*Flower coloration*.—Matched to R.H.S. Greyed-Orange Group #163D.

*Pollen coloration*.—Cream. The remainder of the flower characteristics are typical of the Genus.

General appearance of entire plant:

*Early spring*.—Flush of growth produces relatively large leaves.

*Summer*.—Leaves are much reduced in size on new growth.

*Autumn*.—Many small, almost bract-like leaves along broom-like branches. Most large leaves being deciduous before or at flowering.

Plants of the new variety have been found to grow at a rate of 12 inches during one year under landscape growing conditions with an irrigation system, the new variety reaches maturity in two to three years. At three years of age 'Starn' is four feet in height and six feet in width when grown in Glendale, Ariz. During the blooming season, October through November in Glendale, Ariz., the staminate flowering new variety produces and disperses no pappus from the maturing capitula. In addition, the new variety produces no seeds to produce unwanted volunteer seedlings.

What is claimed is:

1. A new and distinct variety of Baccharis plant as herein illustrated and described.

* * * * *